United States Patent [19]

Antonik

[11] 4,001,088
[45] Jan. 4, 1977

[54] METHOD FOR THE DETERMINATION OF CREATINE PHOSPHOKINASE ENZYME

[76] Inventor: Alan S. Antonik, 599 Exmoor Road, Elk Grove Village, Ill. 60007

[22] Filed: Aug. 2, 1974

[21] Appl. No.: 493,874

[52] U.S. Cl. .......................... 195/103.5 R; 195/99
[51] Int. Cl.² .................... C12K 1/04; G01N 33/00
[58] Field of Search .......... 195/103.5 R; 23/253 TP

[56] References Cited

UNITED STATES PATENTS

| 3,403,077 | 9/1965 | Beyer et al. | 195/103.5 R |
| 3,485,724 | 12/1969 | Beyer et al. | 195/103.5 R |

OTHER PUBLICATIONS

B. L. Strehler et al., "Firefly Luminescence in the Study of Energy Transfer Mechanisms, I. Substrate and Enzyme Determination", Arch Biochem. Biophysics 40, pp. 28–41, 1952.
H. U. Bergmeyer "Methods of Enzymatic Analysis", pp. 559–572, Academic Press, N.Y. and London, 1965.
Dalal et al., Clin. Chem., vol. 18, No. 4, pp. 330–334, 1972.

*Primary Examiner*—A. Louis Monacell
*Assistant Examiner*—C. A. Fan
*Attorney, Agent, or Firm*—Michael G. Berkman; Glenn E. Klepac

[57] ABSTRACT

A method for the detection and the quantitative determination of the enzyme creatine phosphokinase (CPK), an agent present in abnormal concentrational levels in serum in many cases of mental disorders and neuromuscular disorders, and significant in the diagnosis of myocardial infarction. The method utilizes a dried time-stable sample of a pure or mixed component such as a blood-impregnated carrier substance, obviating the need for separatory procedures (i.e., separating the serum from the blood cells) and special handling (i.e. freezing, freeze drying, etc.) to preserve the sample. The mechanism of the laboratory determination is that adenosine diphosphate (ADP) reacts with creatine phosphate in the presence of creatine phosphokinase and magnesium ions to produce adenosine triphosphate (ATP) plus creatine. The ATP, in turn, reacts with the luciferin and luciferase of the firefly lantern system to produce light (bioluminescence), the intensity of which is proportional to the concentration of CPK initially present. There is provided a test reagent system for carrying out the method of the invention.

1 Claim, No Drawings

METHOD FOR THE DETERMINATION OF CREATINE PHOSPHOKINASE ENZYME

BACKGROUND OF THE INVENTION, AND ITS UTILITY

This invention relates to the detection and quantification of serum enzymes in living organisms. The term, serum enzyme, as used herein is meant to include those enzymes occurring normally in the serum, but whose concentration will depend upon or be affected by some pathological condition in the organism, as well as those enzymes not detected in the serum of a normal organism but whose concentration increases under pathological conditions. More particularly, the invention relates to the detection and quantification of the serum enzyme Creatine Kinase (EC2.7.32 International Union of Biochemistry), commonly known as Creatine Phosphokinase or CPK (referred to as CPK hereinafter). The invention teaches the detection of this enzyme in dried samples contained in a porous carrier such as filter paper.

The sample is conveniently obtained from any fluid derived from an organic source such as blood, plasma, serum, spinal fluid, organ extracts, tissue fluid, eye tears, body secretions, tissue cultures etc. Studies in the inventor's laboratory and by others have shown the substrate-carried dried sample to be stable for at least one month under normal ambient conditions.

CPK determination is extremely valuable in the detection of neuromuscular disorders (Munsat et al., *Journal of the American Medical Association*, 226-13, Page 1536, Dec. 24, 1973). The measurement of CPK is also of significant value in the diagnosis of myocardial infarction. There is also growing evidence of abnormal levels of CPK present in many cases of mental disorders. Munsat has further shown that abnormally high CPK levels are present in many carriers of Duchenne Muscular Dystrophy (DMD) and tend to be higher in infancy and adolescence.

Detection of preclinical cases of neuromuscular disorders will facilitate a program of early treatment which can result in prolonged mobility. (Demos, Early Diagnosis and Treatment of Rapidly Developing Duchenne DeBologne-type Myopathy (Type DDB 1); *Am. Jour.Phys.Med.* 50–6, page 271, 1971). Demos has demonstrated that CPK is already present in very high amounts in newborn victims of Duchenne Muscular Dystrophy. Duchenne Muscular Dystrophy occurs in a frequency of about 1 in 3500 male births with a similar ratio for carriers (females). (Morton and Chung, Formal Genetics of Muscular Dystrophy, *Am. Jour.Hum. Gen.* 11–4, page 360, Dec., 1959). It also appears that the disease has a mutation rate of about 35%. The method and reagents described herein have been shown to be capable of detecting Duchenne muscular dystrophy preclinically and have also been shown to be capable of detecting the CPK elevations associated with carriers of this disease.

The methods and reagents of the invention are also useful in detecting abnormal levels of CPK in hamsters and pigs. In the 14:6 strain of the Golden Syrian Hamster, this method is extremely valuable as these are cardio-myopathic animals. As such, a non-destructive CPK test (and this is the first such test developed) is invaluable for monitoring the effectiveness of treatment of these animals for cardio and muscular disease using various chemical compounds. In pigs, CPK has been shown to be elevated to significant levels in animals affected by Porcine Stress Syndrom, a disease which causes poor quality pork and substantial losses of pigs due to death in shipment to market.

SUMMARY OF THE INVENTION

Applicant is believed to be the first to have discovered a practical technique for demonstrating CPK activity, or any other serum enzyme, from an ambient-air-dried state. Erythrocytic enzymes such as glucose-6-phosphate dehydrogenase have been determined from dried blood cells but, previously, serum enzymes have required freeze drying of the serum for long-term stability. Of all the currently popularly used serum enzymes, CPK has had a known history of instability and vulnerability to physical conditions (Dalal, F. R. et al, *Clin. Chem.* 18, No. 4, 1972). In accordance with the practice of the present invention, it is now possible to assay CPK as well as other serum enzymes from an air dried state using appropriate methods.

The method of the invention is based on the principle that CPK in the presence of creatine phosphate and adenosine diphosphate (ADP) [(inosine diphosphate (IDP) cytidine diphosphate (CDP), Uridine disphosphate (UDP) and Guanosine disphosphate (GDP) may replace ADP, in decreasing activity] will produce ATP and creatine (See Reaction A below, in the reverse direction). The mechanism is indicated schematically in reversible equilibria diagrammed as Reaction A and Reaction B, below:

REACTION A:

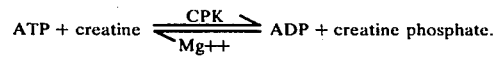

Magnesium is required and the reaction is greatly enhanced by a sulfhydryl group. Other ions may be substituted for magnesium, such ions including manganese, Mn++. The ATP then reacts with the luciferin and luciferase (Reaction B) of the firefly system or in the firefly extract to produce light. The intensity of the light is proportional to the concentration of CPK in the initial reaction system.

REACTION B:

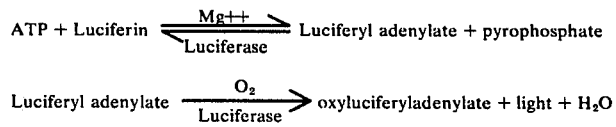

After a short incubation period, the light intensity is measured by means of a photometer or equivalent instrument, the greater the original concentration of CPK present, the greater being the production of light.

Bioluminescent reactions of the general type herein relied upon, between andenosine triphosphate ATP and firefly lantern extract are known and have been utilized in the prior art. Such a light emission phenomenon is described in Chappelle U.S. Pat. Nos. 3,575,811 and 3,575,812 which disclose methods for the measurement of ATP in tissue cultures as a technique for detecting the presence of cancerous cells and/or the presence or absence of a virus in a host cell. Chappelle points out that cancerous cells cause lesser light emission than do normal cells (U.S. Pat. No. 3,575,811) and that the ATP content of virus-containing cells is different from the content of ATP in normal cells (U.S. Pat. No. 3,575,812). However, the Chappelle methods are carried out using conventional tissue cultures and involve laboratory techniques, reagents and reactions which differ materially and significantly from those of the present invention. However, the disclosures of the Chappelle patents are hereby incorporated herein by reference to the extent they are not inconsistent herewith.

In accordance with the practice of the method of the invention meaningful increases in the concentration of a serum enzyme are readily detected in each of a series of pathological conditions. Typical date indicative of metabolic malfunction in organisms are set forth in the following table for types of mental and neuromuscular disorders which are readily detectable using the techniques of the present invention. In the tabular presentation, the "Disorder" appears in the first column. The second column gives the concentration of CPK in International Units, 50 units being the usual upper limit for a normal human. The relative light units (using an Aminco Chem-Glow Photometer) are shown in the third column, 18 units being about the normal upper limit for a normal human.

DETAILED DESCRIPTION OF METHOD $10 \pm 2$ grams of freeze-dried firefly lanterns (Freeze-dried firefly lanterns are available commercially.) are used for every 1000 ml of stock reagent and 3000 ml of working reagent. The firefly lanterns are ground to a fine powder with a mortor and pestle or other grinding apparatus. An "acetone powder" may also be used. (Such a powder is prepared by washing the firefly lantern powder with acetone, filtering and drying.) The material is then extracted with 1000 ml (one liter) of a 0.1M morpholinopropane sulfonic acid (MOPS) buffering agent adjusted to a pH 7.3 with NaOH (sodium hydroxide). The concentration of the buffer may vary by at least from 0.01 to 0.5 M and a variety of other buffers may also be used, such as hydroxymethyl aminomethane and potassium arsenate. In fact, water may be used and adjusted with NaOH to a pH of 7.4. The pH may vary within a range from about 6.8 to 7.8.

A chelating agent such as ethylenedinitrilo tetraacetic acid (EDTA) at a concentration of about 0.001 M may be used, but is not necessary. The solution (firefly powder, buffer, water and chelating agent) is then centrifuged at 10,000 g for 15 minutes. The speed and time may vary and other separation methods may be used.

Alternative methods for preparing the luciferase-luciferin solution include the following:

1. Use of crystallized luciferase as described by Green and McElroy (Green, A. A. and McElroy, W. D., Biochem.Biophys.Acta., 20,170 (1956).

2. Use of a synthetic luciferin which is available commercially.

3. Use of partially purified luciferin-luciferase solutions prepared by various means such as column chromatography.

| TYPICAL LIGHT UNIT READINGS ANTONIK CPK SCREEN | | |
|---|---|---|
| Disorder | Reference Method CPK International Units (Rosalki Method) e.g. 50-Upper limit of normal human | Relative Light Units (Aminco Chem-Glow Photometer) |
| 1. Duchenne Muscular Dystrophy (pre-clinical) | 4000 | 1860 |
| 2. Duchenne Muscular Dystrophy (initial clinical stages) | 3200 | 1500 |
| 3. Duchenne Muscular Dystrophy (medium stages) | 2000 | 1200 |
| 4. DMD (advanced Stage) | 400 | 300 |
| 5. Carrier DMD | 100 | 32 |
| 6. Limb-Girdle Dystrophy | 180 | 36 |
| 7. Facio-Scapulo Humeral | 120 | 33 |
| 8. Schizophrenia | 180 | 36 |
| 9. Myocardial Infarction | 400 | 56 |
| 10. Myositis | 3000 | 1450 |
| 11. Porcine Stress Syndrome | 3000 | 1450 |
| 12. Cardio myopathic Golden Syrian Hamster 14:6 strain | 2800 | 1400 |
| 13. Normal Human | 25 | 12 |
| 14. Normal Pig | 100 | 25 |
| 15. Normal Hamster | 12 | 8 |

A 100 ml buffer solution is prepared using the same procedure as in the above primary extraction. To this solution magnesium ions are added in the form of magnesium acetate, although other organic and inorganic magnesium salts may also be used. The optimum concentration for Mg++ is 0.02M but the range may extend from 0.002 M to 0.1 M. Chloride and phosphate ions are avoided as these have an inhibitory effect on the overall reaction.

To the above solution is added a sulfhydryl compound such as dithiothreitol, (DTT) dithioerythritol or other such compounds such as glutathione, at a concentration of from about 0.1 to 8 mM, with 1mM preferred. The sulfhydryl compound serves to activate the CPK as well as to stabilize the luciferase. This buffer solution is added to the primary extraction and the resulting solution (luciferin-luciferase extract, buffer, magnesium ions, and sulfhydryl compound) is the stock solution and can be freeze dried in appropriate amounts. The resulting product is referred to as Reagent I. For every 1.0 ml of the stock reagent I, 2.0 ml of distilled water is added to prepare the working reagent.

A second reagent is prepared in the same buffer and pH as used above and 0.1M creatine phosphate is added. One part of Reagent II is used to 4 parts of Reagent I to yield a .02 M concentration of creatine phosphate in the final solution. The final concentration may vary from 0.005M to 0.05M. This second reagent (Reagent II) may be divided into appropriate amounts and freeze dried.

TEST METHODS

The test sample may be plasma, serum or whole blood, etc. which is dropped or spotted onto a porous material such as filter paper. The sample is allowed to air dry. It is properly identified and thereafter can be sent by ordinary mail to a centralized test laboratory from any point in the world.

A. WHOLE BLOOD METHOD (or samples containing indigenous ATP):

The following example in no way limits the volumes, sizes, time or temperature:

1. A ⅛ inch paper punch is used to obtain a ⅛ inch diameter disc from the sample material. The disc is placed in a 6 × 50 mm glass tube.
2. 0.2 ml of the working Reagent I is added.
3. During the first hour, the tube is agitated to facilitate the elution of the sample from the substrate material.
4. The tube is allowed to incubate 20 hours after Reagent I is added to the sample at 22° C. During this time, adenosine triphosphate (ATP) is converted to other products by the excess luciferase with at first an increase and then a decrease in light as the ATP is "consumed".
5. After 20 hours, the intensity of light reaches a base line and 0.05 ml of Reagent II is added and the sample is agitated to ensure uniform mixing.
6. 30 minutes after the addition of Reagent II, the tube is placed in a photometer (such as the CHEM-GLOW instrument manufactured by American Instrument Company) and the light intensity is measured.
7. The CPK value is determined from a reference curve constructed from blood with known CPK values as determined by known standard CPK assay methods on plasma portions of the reference blood samples.

B. SERUM AND PLASMA METHOD (or samples containing no, or negligible amounts of ATP)

The following example in no way limits the volumes, sizes, time or temperature:

1. A ⅛ inch paper punch is used to obtain a ⅛ inch diameter disc from the sample material. The disc is placed in a 6 × 50 mm glass tube.
2. 0.2 ml of working Reagent I and 0.05 ml of Reagent II are added to the tube and agitated to ensure uniform mixing.
3. The tube is allowed to incubate at 22° C for 15 minutes and read in a photometer (such as the aforementioned CHEM-GLOW).
4. The CPK value is determined from a light-intensity reference curve constructed from serum or plasma with known CPK values as determined by known standard CPK assay methods.

While this invention has been described with reference to preferred embodiments and procedures, it is evident that the invention is not limited thereto. Further modifications of the method and products disclosed herein which fall within the scope of the following claims will be immediately evident to those skilled in the art. To the extent that these changes and modifications are within the scope of the appended claims, they are to be considered a part of this invention.

What is claimed is:

1. A test reagent useful for the quantitative determination of the enzyme creatine phosphokinase in an organism, thereby to ascertain the presence of normal and pathologically significant excessive concentrational levels of the enzyme in the organism,
    said reagent being operative to produce upon addition to and reaction with specimens of dried blood and dried tears measurable bioluminescent light the intensity of which is a determinable function of the concentration of creatine phosphokinase contained in the specimens, said reagent consisting essentially of:
    a. firefly lantern extract and
    b. creatine phosphate.

* * * * *